United States Patent
Keikert

(10) Patent No.: US 12,251,374 B2
(45) Date of Patent: Mar. 18, 2025

(54) FAMPRIDINE TTS

(71) Applicant: LTS Lohmann Therapie-Systeme AG, Andernach (DE)

(72) Inventor: Rosemarie Keikert, Andernach (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 897 days.

(21) Appl. No.: 16/629,608

(22) PCT Filed: Jul. 12, 2018

(86) PCT No.: PCT/EP2018/068952
§ 371 (c)(1),
(2) Date: Jan. 9, 2020

(87) PCT Pub. No.: WO2019/012047
PCT Pub. Date: Jan. 17, 2019

(65) Prior Publication Data
US 2020/0237682 A1    Jul. 30, 2020

(30) Foreign Application Priority Data

Jul. 12, 2017  (DE) .................. 10 2017 115 701.8

(51) Int. Cl.
*A61K 9/70* (2006.01)
*A61K 31/4409* (2006.01)

(52) U.S. Cl.
CPC ........ *A61K 31/4409* (2013.01); *A61K 9/7069* (2013.01)

(58) Field of Classification Search
CPC .............. A61K 31/4409; A61K 9/7069; A61K 9/7053; A61K 9/7061; A61P 25/28
See application file for complete search history.

(56) References Cited

U.S. PATENT DOCUMENTS

| | | | | |
|---|---|---|---|---|
| 5,370,879 A | * | 12/1994 | Masterson | A61K 31/44 424/494 |
| 5,508,038 A | * | 4/1996 | Wang | A61K 9/7084 424/448 |
| 6,139,868 A | * | 10/2000 | Hoffmann | A61K 9/7061 424/448 |
| 2004/0241219 A1 | * | 12/2004 | Hille | A61P 15/12 424/449 |
| 2013/0053420 A1 | * | 2/2013 | Wessel | A61K 31/44 546/311 |
| 2014/0330223 A1 | * | 11/2014 | Schurad | B32B 37/26 604/290 |
| 2015/0111930 A1 | * | 4/2015 | Aung-Din | A61K 31/4409 514/352 |
| 2016/0151339 A1 | | 6/2016 | Ghanbari | |

FOREIGN PATENT DOCUMENTS

| | | |
|---|---|---|
| CN | 101326275 A | 12/2008 |
| CN | 102088992 A | 6/2011 |
| CN | 102143687 A | 8/2011 |
| CN | 102442942 A | 5/2012 |
| CN | 104220072 A | 12/2014 |
| EP | 2 676 663 A2 | 12/2013 |
| JP | H4-273820 A | 9/1992 |
| JP | 2015 110 539 A | 6/2015 |
| JP | 2016 037 464 A | 3/2016 |
| WO | 03/017988 A1 | 3/2003 |
| WO | 2008/056207 A1 | 5/2008 |
| WO | 2009/107476 A1 | 9/2009 |
| WO | 2013/081102 A1 | 6/2013 |

OTHER PUBLICATIONS

H.S. Tan et al., "Pressure-sensitive adhesives for transdermal drug delivery systems," PSTT vol. 2, No. 2, Feb. 1999, pp. 60-69.*
Liu, P. et al. Novartis (1997), "A Novel Method for Measuring Solubility of a Drug in an Adhesive," Pharmaceutical Research 14, p. 317.
Wiedersberg et al., "Transdermal drug delivery: 30+ years of war and still fighting!" Journal of Controlled Release, 190 (2014), pp. 150-156.
Dow: Dow Corning® BIO-PSA Amine-Compatible Silicone Adhesives. [accessed: Aug. 6, 2018]. URL: http://www.healthcare-plus.com.tw/big5/pdf/02-02.pdf.
Kim, J-H., et al., "Effect of vehicles and pressure sensitive adhesives on the permeation of tacrine across hairless mouse skin," International Journal of Pharmaceutics, vol. 196, (2000), pp. 105-113.
Kokubo, T., et al., "Diffusion of drug in acrylic-type pressure-sensitive adhesive matrices. I. Influence of physical property of the matrices on the drug diffusion," Journal of Controlled Release, vol. 17(1), 1991, pp. 69-77.

(Continued)

*Primary Examiner* — Mina Haghighatian
*Assistant Examiner* — Janice Y Silverman
(74) *Attorney, Agent, or Firm* — ProPat, LLC; Cathy Moore

(57) ABSTRACT

The present invention relates to a transdermal therapeutic system for cutaneous administration of fampridine. The system includes an active ingredient-impermeable backing layer, a pressure-sensitive adhesive reservoir layer and optionally a detachable protective layer. The pressure-sensitive adhesive reservoir layer is formed from fampridine and at least one matrix polymer containing no free carboxylic acid and/or carboxylate groups, with the content of fampridine in the matrix polymer being <5% by weight. On account of the low loading and also the lack of carboxylic acid and/or carboxylate groups in the reservoir layer, it is ensured that the systems administer the active ingredient substantially at higher administration rates than is known in the prior art, and compared to known systems a comparable thermodynamic activity of the active ingredient is achieved. The present invention further relates to a process for producing corresponding transdermal therapeutic systems.

16 Claims, No Drawings

(56) References Cited

OTHER PUBLICATIONS

Kokubo, T., et al., "Interaction Between Drugs and Pressure-Sensitive Adhesives in Transdermal Therapeutic Systems," Pharmaceutical Research, vol. 11, (1994), pp. 104-107.

Morimoto, Yasunori, et al. "Diffusion of drugs in acrylic-type pressure-sensitive adhesive matrix. II. Influence of Interaction," Journal of Controlled Release, vol. 18, 1992, pp. 113-121.

Subedi, R. K., et al., "Formulation and Evaluation of Transdermal Patch Containing Sibutramine," Journal of Pharmaceutical Investigation, vol. 40, No. 1, (2010), pp. 33-38.

Liu, C. et al. "A systemic evaluation of drug in acrylic pressure sensitive adhesive patch in vitro and in vivo: The roles of intermolecular interaction and adhesive mobility variation in drug controlled release," Journal of Controlled Release, vol. 252, Mar. 6, 2017, pp. 83-94.

Hock, S. et al. "Pressure-sensitive adhesives for transdermal drug delivery systems," Pharmaceutical Science & Technology Today, vol. 2, No. 2, Feb. 1, 1999, pp. 60-69.

Henkel Ltd. "DURO-TAK and GELVA Transdermal Pressure Sensitive Adhesives," Product Selection Guide, UK, Sep. 3, 2013, pp. 1-2.

Internation Search Report of WO 2019/012047, which corresponds to PCT/EP2018/068952.

Office Action, JP Patent Application No. 2020-501354, Issued May 31, 2021, with English translation.

Liu et al., "A systemic evaluation of drug in acrylic pressure sensitive adhesive patch in vitro and in vivo: The roles of intermolecular interaction and adhesive mobility variation in drug controlled release," Journal of Controlled Release, vol. 252, Apr. 28, 2017, pp. 83-94, English abstract.

Semba, et al., "4-Aminopyridine induces expansion of cutaneous receptive fields of dorsal horn cells," Brain Research, vol. 343, No. 2, Sep. 23, 1985, pp. 398-402.

Tan, et al., "Pressure-sensitive adhesives for transdermal drug delivery systems" Pharm Sci Technol Today, Feb. 1999; vol. 2, No. 2, pp. 60-69.

Office Action in corresponding CN Application No. 201880046222.3, issued Jan. 5, 2023.

Notice of Allowance in corresponding CN Application No. 201880046222.3, issued Nov. 13, 2023.

* cited by examiner

FAMPRIDINE TTS

CROSS-REFERENCE TO RELATED APPLICATIONS

This application is being filed under 35 U.S.C. § 371 as a National Stage Application of pending International Application No. PCT/EP2018/068952, filed July 12. 2018, which claims priority to the following parent application: German Patent Application No. 10.2017 115 701.8. filed Jul. 12, 2017. Both International Application No. PCT/EP2018/068952 and German Patent Application No. 10 2017 115 701.8 are hereby incorporated by reference herein in their entirety:

FIELD OF THE INVENTION

The invention relates to a transdermal therapeutic system for administration of fampridine comprising an active ingredient-impermeable backing layer, a pressure-sensitive adhesive reservoir layer and optionally a detachable protective layer, and to a process for producing same.

BACKGROUND OF THE INVENTION

Fampridine (4-aminopyridine) reversibly inhibits a large number of potassium channels in nerve cells. The active ingredient intercepts the action potential of a nerve and can thus suppress neurological symptoms of multiple sclerosis (MS) in patients; especially, disruptions to the ability to walk can be improved by treatment with fampridine.

Multiple sclerosis is a chronic inflammatory disease of the central nervous system, which can affect the brain, the spinal cord, or the optic nerves. The cause of this disease is assumed to be an autoimmune reaction. Inflammatory and immune cells of the body mistakenly attack the body's own structures. This leads to a breakdown of the enveloping layer of nerve fibres (myelin sheath) and results in damage to the nerve fibres themselves, with the result that neural stimuli are not forwarded as effectively in the affected fibres. In its normal function, the enveloping layer surrounds the nerve axons similarly to an insulation layer of an electrical cable, and is essential for ensuring that the nerve pulses reach the desired location with a suitable speed. This is no longer possible if the enveloping layer is damaged.

Fampridine is authorised, inter alia, in the USA, Australia and Germany as a drug for the treatment of multiple sclerosis. The drug is sold in tablet form under the trade name FAMPYRA®, which generally must be taken twice daily in a dose of 10 mg. The disadvantages of this administration form are that the patient must take the tablets at regular intervals, and it is difficult to maintain a uniform level of the active ingredient in the body.

Transdermal therapeutic systems (TTS), in recent years, have become a widespread administration form for the treatment of numerous diseases, since they are associated with advantages in comparison to conventional administration forms. These advantages lie, inter alia, in a precise and constant delivery of the active ingredient, which is necessary in order to achieve a constant concentration of the active ingredient in the blood plasma. In addition, the first-pass effect can be avoided and the compliance can be increased, since the patient does not have to take tablets regularly. An advantage of transdermal therapeutic systems in comparison to other topical application systems, such as ointments or creams, lies in the fact that they can be applied over an exact area and thus with an accurate dose, and there is no risk of an accidental smearing of the ointment and contamination of other areas of the skin. In addition, ointments or tablets have to be applied regularly, since it is not generally possible to provide a delayed release of the active ingredient.

It has been assumed for some years now that use of active ingredients in transdermal therapeutic systems is unproblematic, and therefore this application form can be utilised for a large variety of active ingredients. This has been found, however, in recent years to be a misconception, because the molecular transport of active ingredients via the skin constitutes a limiting factor. The transport via the outer skin layer of the stratum corneum is too slow for many active ingredients, and therefore it is not possible to achieve effective delivery and thus an effective concentration of the active ingredient in the blood plasma. At commercial level, the delivery of active ingredients via transdermal therapeutic systems is therefore limited to a few, very potent active ingredients. An overview in this regard can be found for example in Wiedersberg et al., J. Controlled Release, 190 (2014), pages 150-156.

JP 2015 110 539 describes a transdermal therapeutic system that contains 4-aminopyridine as active ingredient. The transdermal therapeutic system contains, in the pressure-sensitive adhesive reservoir layer, 5 to 20% by weight fampridine, whereas the matrix polymer should have a minimum content of carboxylate groups, relative to the active ingredient, of 0.13. In contrast for example to matrix polymers with hydroxy groups, an improved stability of the active ingredient should result due to the carboxyl groups. In addition, a strong fluctuation of the delivery rates over time has been observed for matrix polymers that contain hydroxy groups.

A problem of the above-described teaching lies in the very high active ingredient concentration (5 to 20% by weight) in the delivery system. This is caused by the carboxyl groups in the matrix polymer, which indeed, on the one hand, allow an improved solubility of the active ingredient in the matrix polymer (via salt formation with the amine unit), but on the other hand impede full delivery of the active ingredient to the skin, such that a pharmaceutically active delivery level is undershot, although the TTS still contains significant amounts of active ingredient.

The high active ingredient content is associated with disadvantages in a transdermal therapeutic system. These disadvantages lie in the fact that more active ingredient is required for the production, and that the used patch still contains a relatively large amount of active ingredient, which has to be disposed of. In addition, it is sought to avoid high active ingredient contents in transdermal therapeutic systems also for reasons of pharmaceutical drug safety. A transdermal therapeutic system with low active ingredient content would thus be more economical, friendlier to the environment, and safer.

The aim of the invention is therefore to develop a transdermal therapeutic system for delivering fampridine, the active ingredient content of which is low, and in which fampridine is released from the TTS as fully as possible over the intended delivery period.

SUMMARY OF ADVANTAGEOUS EMBODIMENTS OF THE INVENTION

The aim is addressed in accordance with the invention by a transdermal therapeutic system that comprises an active ingredient-impermeable backing layer, a pressure-sensitive adhesive reservoir layer, and optionally a detachable protective layer, wherein the pressure-sensitive adhesive reservoir layer contains fampridine and at least one matrix polymer, wherein the matrix polymer(s) contain no free carboxylic acid and/or carboxylate groups, and wherein the content of fampridine in the matrix polymer is <5% by weight (specified as active ingredient proportion in the polymer matrix; the active ingredient is present predominantly in dissolved form).

The values in % by weight fampridine relate to the free base fampridine.

The saturation concentration of the base fampridine is lower in a matrix polymer without free carboxylic acid and/or carboxylate groups than in a matrix polymer as used in the prior art. A thermodynamic activity similar to that with use of a matrix polymer with free carboxylic acid and/or carboxylate groups can thus be achieved with a lower active ingredient content.

At the same time it has surprisingly been found that transdermal therapeutic systems according to the invention have a good to sufficient adhesive force, even though there is no use of matrix polymers, especially polyacrylates with carboxyl groups, which provide the polymer with a high inherent tack. This solution is all the more astonishing since fampridine does not have any inherent tack.

In a preferred embodiment the transdermal therapeutic system contains 0.5 to 4% by weight fampridine in the matrix polymer.

In spite of the lower content in comparison to the prior art, the desired daily dose can still be achieved. Advantages in relation to the prior art result from the lower active ingredient requirement for the production of the TTS, the resultant lower production costs, the simpler disposal, and the greater safety.

DETAILED DESCRIPTION OF ADVANTAGEOUS EMBODIMENTS OF THE INVENTION

The active ingredient-impermeable backing layer is constructed from a composite material and comprises a film with aluminium vapour-deposited thereon. The film is based expediently on an active ingredient-impermeable material, wherein polyesters such as polyethylene terephthalate, polybutylene terephthalate, polyethylene naphtholate, polyolefins such as polyethylene or propylene, ethylene vinyl acetate, polyvinyl chloride, polyamide (nylon) or polyurethane can be specified as suitable materials.

With regard to the matrix polymer, the transdermal therapeutic system of the present invention is not subject to any relevant limitations, with the exception of the fact that it does not contain any free carboxylic acid and/or carboxylate groups. The expression "free carboxylic acid and/or carboxylate groups" in the content of the present invention means —$CO_2H$— and —$CO_2^-$— groups which are present in non-bonded and non-complexed form. —$CO_2$— groups that are bonded in the form of esters or coordinate at complex-forming metals, especially transition metals such as titanium, are not considered to be free carboxylic acid and/or carboxylate groups, whereas carboxylate salts with non-coordinating metal ions, such as alkali metal ions or alkaline earth metal ions, shall be considered to be free carboxylate groups within the scope of this description.

In a preferred embodiment the matrix polymer of the reservoir layer comprises linear styrene-butadiene-styrene or styrene-isoprene-styrene block copolymer.

Further suitable matrix polymers are acrylate polymers, especially in the form of self-crosslinking acrylate copolymers of 2-ethylhexylacrylate, vinyl acetate, acrylic acid and titanium chelate ester, in which the acrylic acid bonded to the titanium forms crosslinking points, or non-self-crosslinking acrylate copolymer of 2-ethylhexylacrylate, vinyl aetate and 2-hydroxyethyl acrylate.

A polymer that likewise can be used expediently as matrix polymer is polyisobutylene, which can be used alone or in combination with polybutylene.

Polar vinyl polymers, such as polyvinyl pyrrolidone or polyvinyl alcohol, are also usable as matrix polymers.

Lastly, non-organic polymers such as polysiloxanes can also be used as matrix polymer. It is also possible to use mixtures of the aforementioned polymers as matrix polymer, however this is on the condition that the polymers are sufficiently compatible with one another, such that there is not a substantial segregation of the polymer components. Based on the higher processing effort necessary for the production of reservoir layers based on different polymers, however, it is preferred if the ITS contains only one polymer type as reservoir layer.

The matrix polymer accounts for the greatest proportion in the reservoir layer. The reservoir layer thus generally contains a proportion of matrix polymer in the range of from 70 to 99% by weight, preferably 75 to 97% by weight, and very especially preferably 80 to 95% by weight.

Besides the aforementioned constituents, the reservoir layer may also contain conventional additives. The type of potential additives is dependent on the used polymer and the active ingredient. Depending on their function, these can be divided into plasticisers, tackifiers, stabilisers, carriers, diffusion- and penetration-regulating additives, or fillers. The physiologically safe substances possible in this regard are known to a person skilled in the art. The reservoir layer has such an inherent tack that continuous contact with the skin is ensured.

Examples of suitable plasticisers are diesters of dicarboxylic acids, for example di-n-butyl adipate, and triglycerides, especially medium-chain (i.e. $C_6$-$C_{14}$) triglycerides, for example of coconut oil caprylic/capric acid.

With regard to the above-mentioned additives, it should be noted that these, similarly to the matrix polymer, should have no free carboxylic acid and/or carboxyl groups, since this would be contrary to the purpose of providing the fullest possible release of fampridine from the transdermal therapeutic system. The additives are preferably free from carboxylic acid and/or carboxyl groups.

The detachable protective layer, which is in contact with the reservoir layer and is removed prior to use, for example comprises the same materials as are used for the production of the backing layer, provided that they are made detachable, for example by a silicone treatment. Other detachable protective layers are, for example, polytetrafluoroethylene, treated paper, cellophane, polyvinylchloride, and the like. If the laminate according to the invention is divided into a format suitable for therapy (patches) before the protective layer is applied, the protective layer formats may then have a protruding end, with the aid of which they can be easily removed from the patch.

The application time for which the transdermal therapeutic system is intended is preferably at least 12 hours, more preferably at least 24 hours, and even more preferably at least 48 hours. The active ingredient amount must be coordinated with the desired application time accordingly.

The transdermal therapeutic system according to this invention is preferably configured such that a daily dose of delivered fampridine in the range of from approximately 5 to 50 mg, and preferably from 7 to 25 mg, is achieved. To this end the TTS is made in a suitable size, for example in the range of from 5 to 20 cm².

The transdermal therapeutic system according to the invention is suitable for the treatment of patients suffering from multiple sclerosis. A further aspect of the present invention therefore relates to a transdermal therapeutic system as described above for use in the treatment of multiple sclerosis.

The present invention lastly relates to a process for producing the transdermal therapeutic system according to the invention.

The process for producing an above-described transdermal therapeutic system requires at least the following steps:
applying a solution comprising the matrix polymer, fampridine and at least one pharmaceutically acceptable solvent to a detachable protective layer;
drying the solution so as to form a pressure-sensitive adhesive reservoir layer; and
applying an active ingredient-impermeable backing layer to the pressure-sensitive adhesive reservoir layer.

The pharmaceutically acceptable solvent comprises conventional solvents used for pharmaceutical applications, and mixtures of such solvents.

With regard to the advantages of the process for producing the above-described transdermal therapeutic system, reference is made to the description of the transdermal therapeutic system.

The invention will be explained in greater detail hereinafter on the basis of a practical example.

EXAMPLE 1: DETERMINING THE SATURATION CONCENTRATION $C_S$ OF FAMPRIDINE IN VARIOUS POLYMERS

The saturation concentration $C_s$ of fampridine was determined in various polymer matrices by the method described by Liu. (Liu, P., Gargiulo, P., Wong, J., and Novartis (1997). A Novel Method for Measuring Solubility of a Drug in an Adhesive, *Pharmaceutical Research* 14, page 317).

In this method, known by specialists as the "sandwich" method, the saturation concentration is determined as follows:

A laminate is constructed, having the following layer sequence: protective film—donor layer with active ingredient (dissolved and undissolved)—active ingredient-permeable membrane—acceptor layer without active ingredient—protective film. The two protective films are made of identical material; the matrix material of the donor and of the acceptor layer is likewise identical.

The donor layer is produced by dissolving the active ingredient in a solution of the polymer in organic solvent. The concentration of the active ingredient must be selected to be high enough that an undissolved residue can be identified in the polymer matrix so that the saturation concentration $C_s$ in the donor layer is reliably exceeded. This solution is applied to the protective film, and the process solvent is evaporated. The adhesive surface of the donor layer is then covered with the membrane. A dialysis tube made of regenerated cellulose (ZelluTrans®, from Roth, 46 mm flat width) that has been cut to size in the longitudinal direction is used as membrane. The acceptor layer is produced without active ingredient, similarly to the donor layer, and the membrane is applied to the other side.

The laminates thus produced are then stored for 7 days at room temperature, during which time the active ingredient diffuses through the membrane into the acceptor layer. The active ingredient concentration in the donor layer is then determined. To this end, aliquots of approximately 1 cm² are punched out using a punching tool of standardised area. The membrane is then removed, the punched blanks without membrane are weighed, and their weight is recorded ($m_1$). The punched blanks are then placed in organic solvent so as to remove the matrices. The backing layers are removed, washed, and dried, and their weight ($m_2$) is determined. The two measured values give the weight of the polymer proportion of the acceptor layer $m_3$ as follows:

$$m_3 = m_1 - m_2$$

The concentration of fampridine in the solution is then calculated using an HPLC method, and its concentration in the donor layer is calculated. The saturation concentrations of fampridine in different polymer matrices determined on the basis of this test approach are summarised in Table 1:

TABLE 1

$C_s$ of fampridine in different polymer matrices

| Polymer | $C_s$ of fampridine [%] | Solvent used to dissolve the polymer |
|---|---|---|
| Polyisobutylene | 2.2 | Toluene |
| Styrene-isoprene-styrene block copolymer | 2.7 | Toluene |
| Acrylate copolymer of 2-ethylhexylacrylate, vinyl acetate and 2-hydroxyethyl acrylate | 3.3 | Ethyl acetate |
| Polysiloxane | 0.3 | Ethyl acetate |
| Acrylate copolymer of 2-ethylhexylacrylate, butyl acrylate, vinyl acetate, acrylic acid | 7.4 | Ethyl acetate |

It is clear from Table 1 that the saturation concentration $C_s$ of fampridine in neutral polymers is approximately 3%, whereas saturation concentrations approximately 3 times higher were determined in acidic polymers. An especially low $C_s$ of fampridine was measured in polysiloxane.

EXAMPLE 2: PRODUCTION OF FAMPRIDINE TTS

Transdermal therapeutic systems based on different base polymers were produced:
a) TTS with Polyisobutylene (PIB)
Production of Polyisobutylene Solution 50 g each of OPPANOL® B 10 and of OPPANOL® B 100 were dissolved in 250 g toluene with stirring over several days. 350 g of solution with 28.6% solids were obtained.
Production of Samples 1, 2 and 3

0.6 g, 0.9 g and 1.2 g fampridine base were scattered into 100 g each of the produced polyisobutylene solution, and several hours passed before the solids had fully dissolved. These three solutions were applied to a 100 μm siliconised. PET film (Mitsubishi RN 100) using an Erikson doctor blade.

Once the toluene had evaporated, the weight per unit area was approximately 90 g/m². The fampridine concentration in sample 1 was 2%, that in sample 2 was approximately 3%, and that in sample 3 was approximately 4%.

b) TTS with Styrene-Isoprene-Styrene (SIS)
Production of Styrene-Isoprene-Styrene Block Copolymer Solution 95 g styrene-isoprene-styrene block copolymer and 5 g abietyl alcohol were dissolved by stirring in 250 g toluene over several days. 350 g of a solution with 28.6% solids were obtained. Since styrene-isoprene-styrene block copolymer is not a pressure-sensitive adhesive, abietyl alcohol was added as tackifying resin.

Production of Samples 4, 5 and 6

0.8 g, 1.2 g and 1.5 g fampridine base were scattered into 1.00 g each of the produced styrene-isoprene-styrene block copolymer solution, and several hours passed before the solids had fully dissolved. These three solutions were applied to a 100 μm siliconised PET film (Mitsubishi RN 100) using an Erikson doctor blade. Once the toluene had evaporated, the weight per unit area was approximately 90 g/m². The fampridine concentration in sample 4 was 2.7%, that in sample 5 was approximately 4%, and that in sample 6 was approximately 5%.

c) TTS with Polyacrylates

Polyacrylates which can be used as medical pressure-sensitive adhesive can be procured commercially as solutions in organic solvents. For samples 7-9, the following trade products from Henkel: DUROTAK® 87-4287—a natural acrylate copolymer of 2-ethylhexylacrylate, vinyl acetate and 2-hydroxyethyl acrylate in ethyl acetate (39% solids content)—and DUROTAK® 387-2051, an acidic acrylate copolymer of 2-ethylhexylacrylate, butyl acrylate, vinyl acetate, and acrylic acid in ethyl acetate/n-heptane (51.5% solids content), were used as reference.

TTS in Neutral Polyacrylate Samples 7, 8 and 9

0.8 g, 1.3 g and 1.6 g fampridine base were scattered into 100 g each of DUROTAK® 87 4287, and several hours passed before the solids had fully dissolved. These three solutions were applied to a 100 μm siliconised PET film (Mitsubishi RN 100) using an Erikson doctor blade. Once the toluene had evaporated, the weight per unit area was approximately 135 g/m². The fampridine concentration in sample 7 was 2%, that in sample 8 was approximately 3.3%, and that in sample 9 was approximately 3.95%.

TTS in Acid Polyacrylate (Reference) Samples 10, 11 and 12

4 g, 6 g and 7 g fampridine base were scattered into 100 g each of DUROTAK® 387 2051, and several hours passed before the solids had fully dissolved. These three solutions were applied to a 100 μm siliconised PET film (Mitsubishi RN 100) using an Erikson doctor blade. Once the solvent had evaporated, the weight per unit area was approximately 90 g/m². The fampridine concentration in sample 1.0 was 7.2%, that in sample 11 was approximately 10.4%, and that in sample 12 was approximately 12%.

d) TTS in Polysiloxane
Production of the Solution of Polysiloxane in Toluene

Fampridine base is sufficiently soluble in aromatic hydrocarbons, but not in n-heptane. Since toluene polysiloxane solution is not commercially obtainable, BIO PSA 4201 from Dow Chemicals (polysiloxane in n-heptane) was used as starting material. The solvent was evaporated and the rubber-like polymer residue was dissolved with so much toluene that a solution with approximately 75% solids was obtained.

Production of Samples 13, 14 and 15

0.25 g, 0.5 g and 1 g fampridine base were scattered into 100 g of the produced toluene polysiloxane solution, and several hours passed before the solids had fully dissolved. These three solutions were applied to a 100 μm siliconised PET film (Mitsubishi RN 100) using an Erikson doctor blade. Once the toluene had evaporated, the weight per unit area was approximately 90 g/m². The fampridine concentration in sample 13 was 0.33%, that in sample 14 was approximately 0.66%, and that in sample 15 was approximately 1.3%.

The active ingredient crystallised in samples 14 and 15.

Permeation Results

Permeation experiments were performed with samples 1-15 in a Franz cell with human skin. The test parameters are summarised in Table 2.

TABLE 2

Test parameters for in vitro permeation

| Permeation area | Punched blank area | Acceptor medium | Water bath temperature | Permeation duration Thickness of the skin |
|---|---|---|---|---|
| Approx. 1.6 cm² | 1.16 | 10 ml physiological saline solution | 32° C. | 24 hours/ approx. 500 μm |

The results of the permeation studies, the absolute contents of fampridine, and the active ingredient utilisation are specified in Table 3.

TABLE 3 mean (x from n = 6) fampridine flux measured on human skin 500 μm in Franz cells over 24 hours

| Sample no./ polymer | Content of fampridine [mg/1.16 cm²] | Cumulative flux in 24 h [mg/24] | Active ingredient utilisation [%] |
|---|---|---|---|
| 1* PIB | 0.21 | 0.087 | 41.4 |
| 2 PIB | 0.31 | 0.177 | 57 |
| 3 PIB | 0.42 | 0.264 | 63 |
| 4 *SIS | 0.28 | 0.083 | 29.6 |
| 5 SIS | 0.42 | 0.191 | 45.5 |
| 6 SIS | 0.52 | 0.22 | 42.3 |
| 7* neutr. PA | 0.31 | 0.082 | 26.4 |
| 8 neutr. PA | 0.52 | 0.163 | 31.3 |
| 9 neutr. PA | 0.62 | 0.278 | 42.8 |
| 10* acidic PA | 0.75 | 0.08 | 10.6 |
| 11 acidic PA | 1.09 | 0.154 | 14.1 |
| 12 acidic PA | 1.26 | 0.23 | 18.3 |
| 13* polysiloxane | 0.04 | 0.017 | 42.5 |
| 14 polysiloxane | 0.07 | 0.04 | 57.1 |
| 15 polysiloxane | 0.13 | 0.047 | 36.2 |

*Fampridine concentration close to the saturation concentration $C_s$

It can be seen from Table 3 that the use of neutral polymer TTS with active areas <40 cm² with use of 1-2 TTS/day makes fampridine available transdermally in daily doses that correspond to the oral daily doses. Samples 3 and 9 are especially suitable.

The invention claimed is:

1. A transdermal therapeutic system for cutaneous administration of fampridine comprising an active ingredient-impermeable backing layer, a pressure-sensitive adhesive reservoir layer and optionally a detachable protective layer, wherein the pressure-sensitive adhesive layer contains fampridine and at least one matrix polymer, wherein the matrix polymer(s) contain no carboxylic acid and/or carboxylate groups, and wherein the content of fampridine in the matrix polymer is <5% by weight and
wherein the size of the transdermal therapeutic system is in the range of from 5 to 20 cm², the matrix polymer(s) ensures continuous skin-contact wherein the fampridine has been dissolved in toluene or ethyl acetate, and the system does not include a tackifier.

2. The transdermal therapeutic system according to claim 1, wherein the content of fampridine in the matrix polymer is 0.5 to 4% by weight.

3. The transdermal therapeutic system according to claim 1, wherein the active ingredient-impermeable backing layer is constructed from a composite material and comprises a film with aluminum vapor-deposited thereon.

4. The transdermal therapeutic system according to claim 1, wherein the matrix polymer contains linear styrene-butadiene-styrene or styrene-isoprene-styrene block copolymer.

5. The transdermal therapeutic system according to claim 1, wherein the matrix polymer contains self-crosslinking or non-self-crosslinking acrylate copolymer of 2-ethylhexylacrylate, vinyl acetate and 2-hydroxylethyl acrylate.

6. The transdermal therapeutic system according to claim 1, wherein the matrix polymer contains polyisobutylene or polybutylene and polyisobutylene.

7. The transdermal therapeutic system according to claim 1, wherein the matrix polymer contains polyvinyl pyrrolidone or polyvinyl alcohol.

8. The transdermal therapeutic system according to claim 1, wherein the matrix polymer contains polysiloxane.

9. The transdermal therapeutic system according to claim 1, wherein said system is designed for an application time of at least 24 hours.

10. The transdermal therapeutic system according to claim 1, wherein said system is designed to deliver a daily dose of fampridine of from approximately 5 to 50 mg.

11. A process for producing a transdermal therapeutic system according to claim 1, comprising the following steps:
applying a solution comprising the matrix polymer and fampridine dissolved in a pharmaceutically acceptable solvent chosen from toluene or ethyl acetate to a detachable protective layer;
drying the solution to form a pressure-sensitive adhesive reservoir layer; and
applying an active ingredient-impermeable backing layer to the pressure-sensitive adhesive reservoir layer.

12. The transdermal therapeutic system according to claim 10, wherein said system is designed to deliver a daily dose of fampridine of from 7 to 25 mg.

13. The transdermal therapeutic system according to claim 1, wherein said system does not comprise a diffusion-regulating or penetration-regulating additive.

14. The transdermal therapeutic system according to claim 1, wherein the matrix polymer does not contain hydroxy groups.

15. The transdermal therapeutic system according to claim 1, wherein said system exhibits an active ingredient utilization ranging from 41.4 to 63%.

16. The transdermal therapeutic system as claimed in claim 1, wherein the pressure-sensitive adhesive layer consists of (i) fampridine, (ii) polyisobutylene matrix polymer and (iii) optional additives consisting of stabilizers, carriers or fillers.

* * * * *